United States Patent [19]
Fujioka et al.

[11] Patent Number: 5,634,917
[45] Date of Patent: Jun. 3, 1997

[54] DISPOSABLE ABSORBENT UNDERGARMENT

[75] Inventors: Yoshihisa Fujioka, Kagawa-ken; Yoshio Ono, Kawanoe, both of Japan

[73] Assignee: Uni-Charm Corporation, Ehime-ken, Japan

[21] Appl. No.: 502,044

[22] Filed: Jul. 13, 1995

[30] Foreign Application Priority Data

| Jul. 14, 1994 | [JP] | Japan | ..................... | 6-162285 |
| Jul. 18, 1994 | [JP] | Japan | ..................... | 6-165317 |

[51] Int. Cl.$^6$ ........................... A61F 13/15; A61F 13/20
[52] U.S. Cl. ................ 604/385.2; 604/394; 604/373
[58] Field of Search ............................... 604/394, 395, 604/396, 385.2, 373

[56] References Cited

U.S. PATENT DOCUMENTS

| 4,808,177 | 2/1989 | DesMarais | ............................. 604/385.1 |
| 4,834,738 | 5/1989 | Kielpikowski et al. | . |
| 4,897,084 | 1/1990 | Ternstrom et al. | . |
| 5,055,103 | 10/1991 | Nomura et al. | ................... 604/385.2 |
| 5,188,627 | 2/1993 | Igaue et al. | ............................ 604/385.2 |
| 5,415,649 | 5/1995 | Watanabe et al. | ................... 604/385.2 |
| 5,447,508 | 9/1995 | Numano et al. | ......................... 604/394 |

FOREIGN PATENT DOCUMENTS

| A-0 437771 | 7/1991 | Japan . |
| 3-186263 | 8/1991 | Japan . |
| 8602530 | 5/1986 | WIPO | ................................. 604/385.1 |

*Primary Examiner*—John G. Weiss
*Assistant Examiner*—Bruce E. Snow
*Attorney, Agent, or Firm*—Lowe, Price, LeBlanc & Becker

[57] ABSTRACT

A disposable absorbent undergarment comprising: leg-hole surrounding elastic members including first and second front-half elastic portions extending primarily along front-halves of first and second leg-hole defining edges, first and second rear-half elastic portions extending primarily along rear-halves thereof, and bridging elastic portion(s) intersecting the first front- and rear-half elastic portions, and the second front- and rear-half elastic portions, respectively, so that these elastic portions may surround the first and second leg-hole defining edges without interruption, respectively.

5 Claims, 10 Drawing Sheets

FIG.IO  PRIOR ART
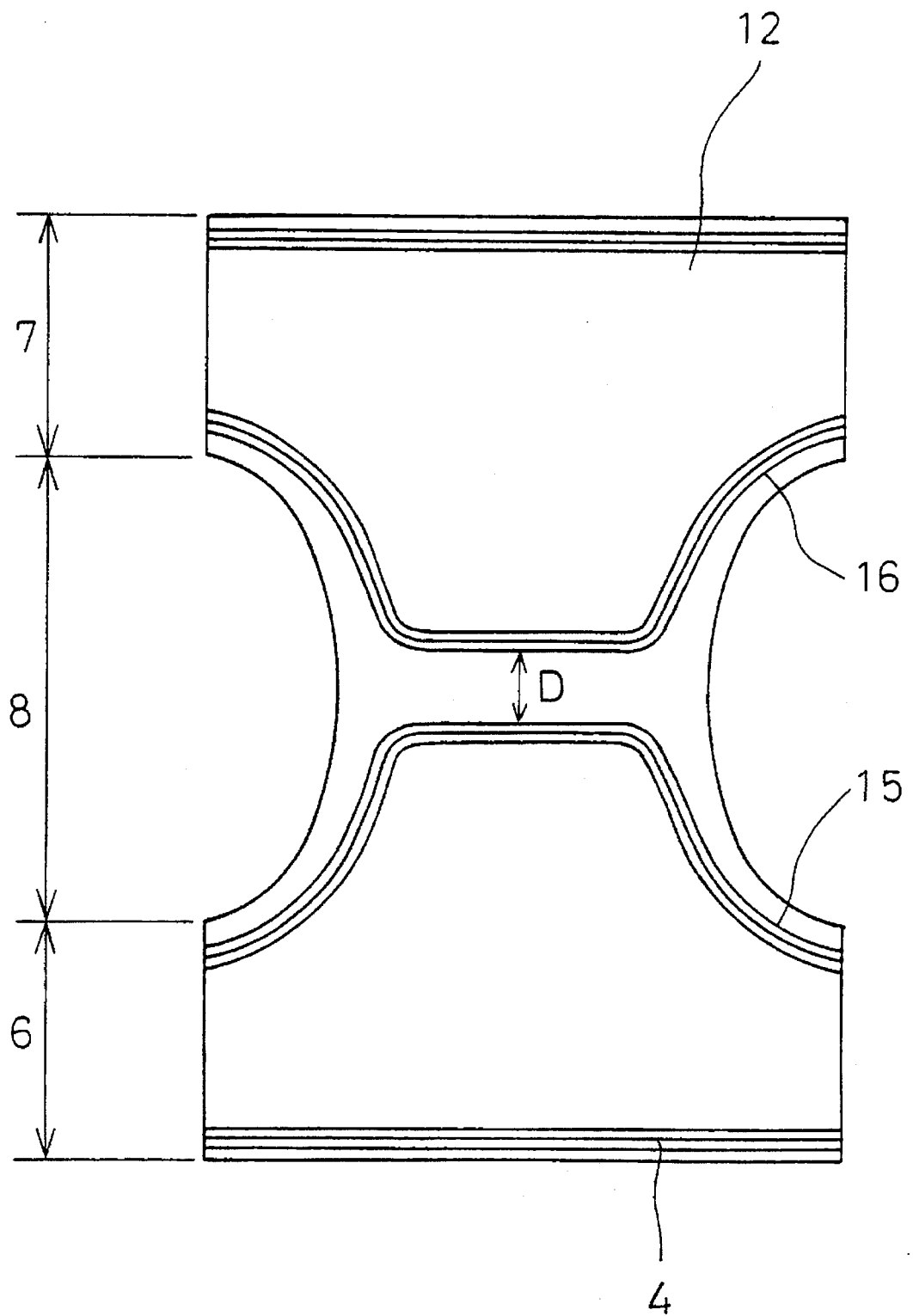

1

DISPOSABLE ABSORBENT UNDERGARMENT

BACKGROUND OF THE INVENTION

The present invention relates to a disposable absorbent undergarment and, more particularly, to an disposable absorbent undergarment such as disposable diapers, incontinent pads, training pants and the like.

It is well known as a usual technique to attach elastic members to the foresaid undergarments around leg-hole defining edges thereof to fit these edges around a wearer's legs. Such technique is well known, for example, from the disclosures of U.S. Pat. No. 4,897,084 and Japanese Laid-Open Patent Application No. Hei 3-186263, according to which these elastic members for the undergarment comprise a first elastic member extending along front-halves of the leg-hole defining edges of undergarment and a second elastic member extending along rear-halves thereof. These well known techniques are said to allow different conditions, for example, the types, the number, the arrangement spaces and the contractile forces of the elastic members, to be adopted for the front-halves and the rear-halves of the leg-hole defining edges to achieve the undergarment having the optimal comfortableness to wear as well as the optimal ability of preventing body fluids from leaking sideways.

According to the disclosure of the above-cited U.S. Pat. No. 4,897,084, the first elastic member extends from transversely central zone of a rear section of the undergarment along the front-halves of the leg-hole defining edges so as to generally described "U" while the second elastic member extends from transversely central zone of a front section of the undergarment along the rear-halves of the leg-hole defining edges so as to generally describe "inverted U", wherein these first and second elastic members intersect each other on a longitudinal center line of a crotch section of the undergarment adjacent the respective leg-hole defining edges so that these first and second elastic members cooperate with each other to surround the respective leg-hole defining edges.

Similarly, according to the above-cited Japanese Laid-Open Patent Application No. Hei 3-186263, the first elastic member is attached to the front-halves and the second elastic member is attached to the rear-halves of the leg-hole defining edges of the undergarment with their longitudinally inner portions intersecting each other in a longitudinally central zone of a crotch section of the undergarment.

FIG. 9 of the accompanying drawings is a plan view exemplarily showing the undergarment according to above-mentioned Japanese Laid-Open Patent Application No. Hei 3-186263, in which first and second elastic members 15, 16 are attached to a backsheet 12 along front-halves and rear-halves of leg-hole defining edges, respectively, and intersect each other at an angle A in a central zone of a crotch section 8. From a state shown by FIG. 9, the undergarment may be folded in two with a front section 6 lying upon a rear section 7 and thereby loops closely surrounding a wearer's legs may be formed by these first and second elastic members 15, 16. However, if the angle A is relatively small, it will be difficult to put the loops closely around the legs in the proximity of the points at which the first and second elastic members 15, 16 intersect each other and body fluids readily leak sideways there. Discharge of body fluids is concentrated in the crotch section and therefore this problem is serious for the undergarment having the elastic members 15, 16 intersecting each other in the crotch section.

FIG. 10 of the accompanying drawings is a plan view showing the undergarment according to the above-mentioned U.S. Pat. No. 4,897,084, in which the first and second leg-hole surrounding elastic members 15, 16 are spaced from each other by a distance D in the central zone of a crotch section 8.

From a state shown by FIG. 10, the undergarment may be folded in two with a front section 6 lying upon a rear section 7 and thereby loops closely surrounding a wearer's legs may be substantially formed by these first and second elastic members 15, 16. However, the first and second elastic members 15, 16 are spaced from each other in the central zone of the crotch zone 8, so it is difficult to put the loops closely around the legs in the proximity of the points at which the first and second elastic members 15, 16 intersect each other and body fluids readily leak sideways there. Discharge of body fluids is concentrated in the crotch section and therefore this problem is also serious the same as the foresaid problem.

The attempt has sometimes been made to increase a contractile force of the elastic members in order to solve this problem. However, this attempt has not been a perfect solution, since the increased contractile force of the elastic members may disturb blood circulation around the legs and deteriorate a comfortableness of the undergarment to wear.

OBJECTS AND SUMMARY OF THE INVENTION

In view of the problems as described above, it is a principal object of the invention to solve the problems by providing an undergarment with third elastic members being stretchable longitudinally of the undergarment and intersecting first and second elastic members extending along front- and rear-halves of leg-hole defining edges, respectively, so that these first, second and third elastic members may cooperate with one another to surround the respective leg-hole defining edges without interruption.

To achieve the object set forth above, the invention broadly resides in a disposable absorbent undergarment comprising: a liquid-permeable topsheet; a liquid-impermeable backsheet; a liquid-absorbent core between the topsheet and the backsheet; a laminate comprising the topsheet, the backsheet and the core and having a front section, a rear section and a crotch section interposed between the front section and the rear section; first and second leg-hole defining edges in the form of generally circular-arc-shaped notches on transversely opposite sides of the crotch section; stretchable elastic members generally extending along each of the first and second leg-hole defining edges; the elastic members comprising first and second front-half elastic portions extending primarily along first and second front-halves halves of the first and second leg-hole defining edges, first and second rear-half elastic portions extending primarily along first and second rear-halves of the first and second leg-hole defining edges, and first and second bridging elastic portion extending longitudinally on transversely opposite sides of the crotch section, the first and second front-half elastic portions connecting with each other in said crotch section, and the first and second rear-half elastic portions connecting with each other in the crotch section, the first bridging elastic portion intersecting the first front- and rear-half elastic portions, and the second bridging elastic portion intersecting the second front- and rear-half portions.

Preferably, the first front- and rear-half elastic portions intersect each other in a longitudinally central zone on one of the transversely opposite sides of the crotch section, the second front- and rear-half elastic portions intersect each other in a longitudinally central zone on the other of the transversely opposite sides of the crotch section, the first bridging elastic portion is positioned outwardly of the intersecting point of the first front- and rear-half elastic portions, and the second bridging elastic portion is positioned outwardly of the intersecting point of the second front- and rear-half elastic portions.

Preferably, the first and second front-half elastic portions and the first and second rear-half portions connect with each other between the first and second bridging elastic portions.

Preferably, the first and second bridging elastic portions are in the form of a single elastic sheet.

Preferably, the front-half elastic portions, the rear-half elastic portions and the bridging elastic portions comprise plural elastic strings.

BRIEF DESCRIPTION OF THE DRAWINGS

FIGS. 9 and 10 are views similar to FIG. 3, exemplarily showing conventional disposable diapers, respectively.

PREFERRED EMBODIMENTS OF THE INVENTION

Figure 1:
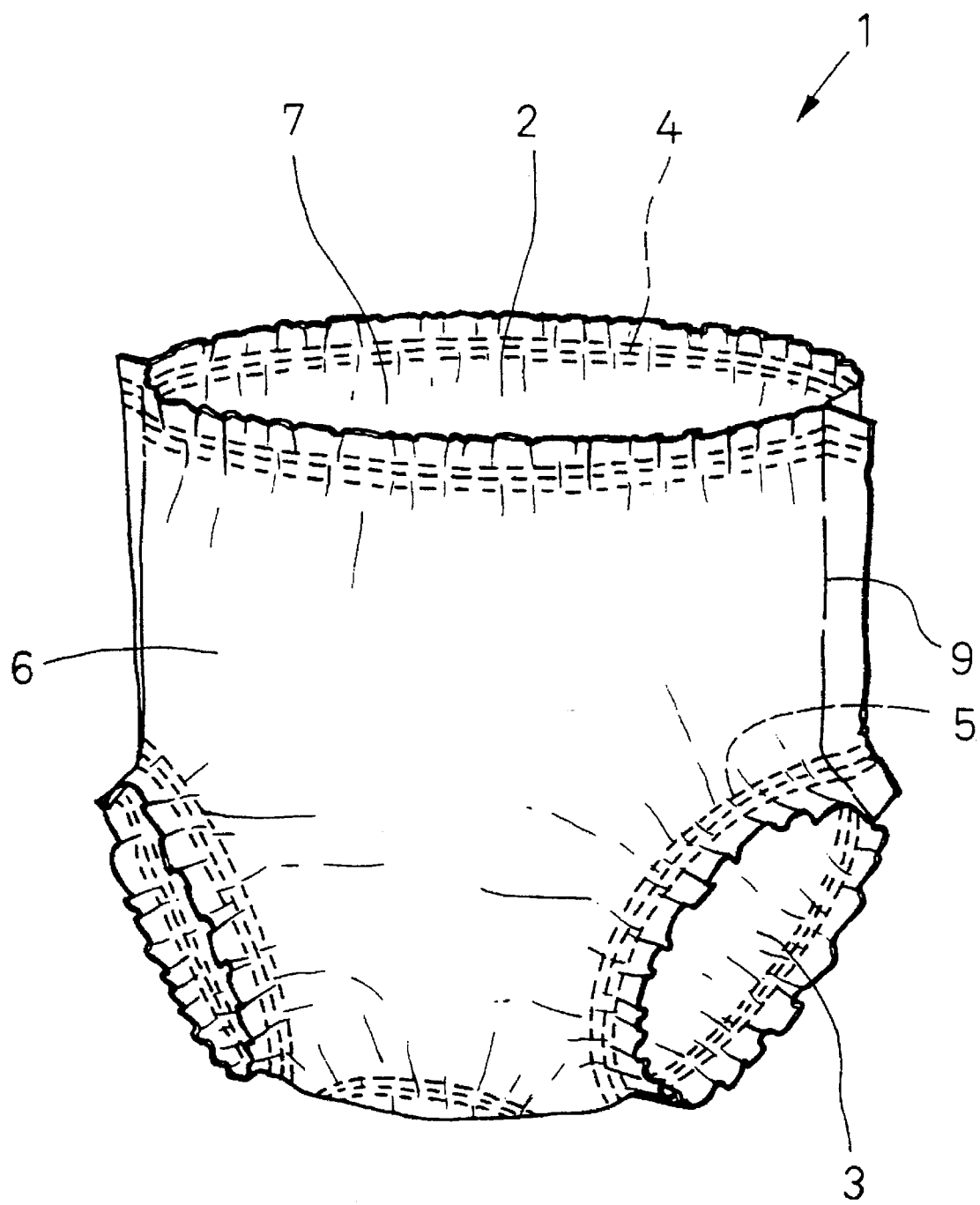
FIG. 1 is a perspective view showing an embodiment of disposable diaper (disposable absorbent undergarment in general) according to the invention.

Referring to FIG. 1, a diaper 1 is in the form of pants type and has a waist-hole 2 and a pair of leg-holes 3. The waist-hole 2 is circumferentially provided with a waist surrounding elastic member 4 and the leg-holes 3 are also circumferentially provided with leg surrounding elastic members 5, respectively. Front and rear bodies defining front and rear sections 6, 7 of the diaper 1 lie one upon another along transversely opposite side edges and are integrally bonded to each other by bonding lines 9.

Figure 2:
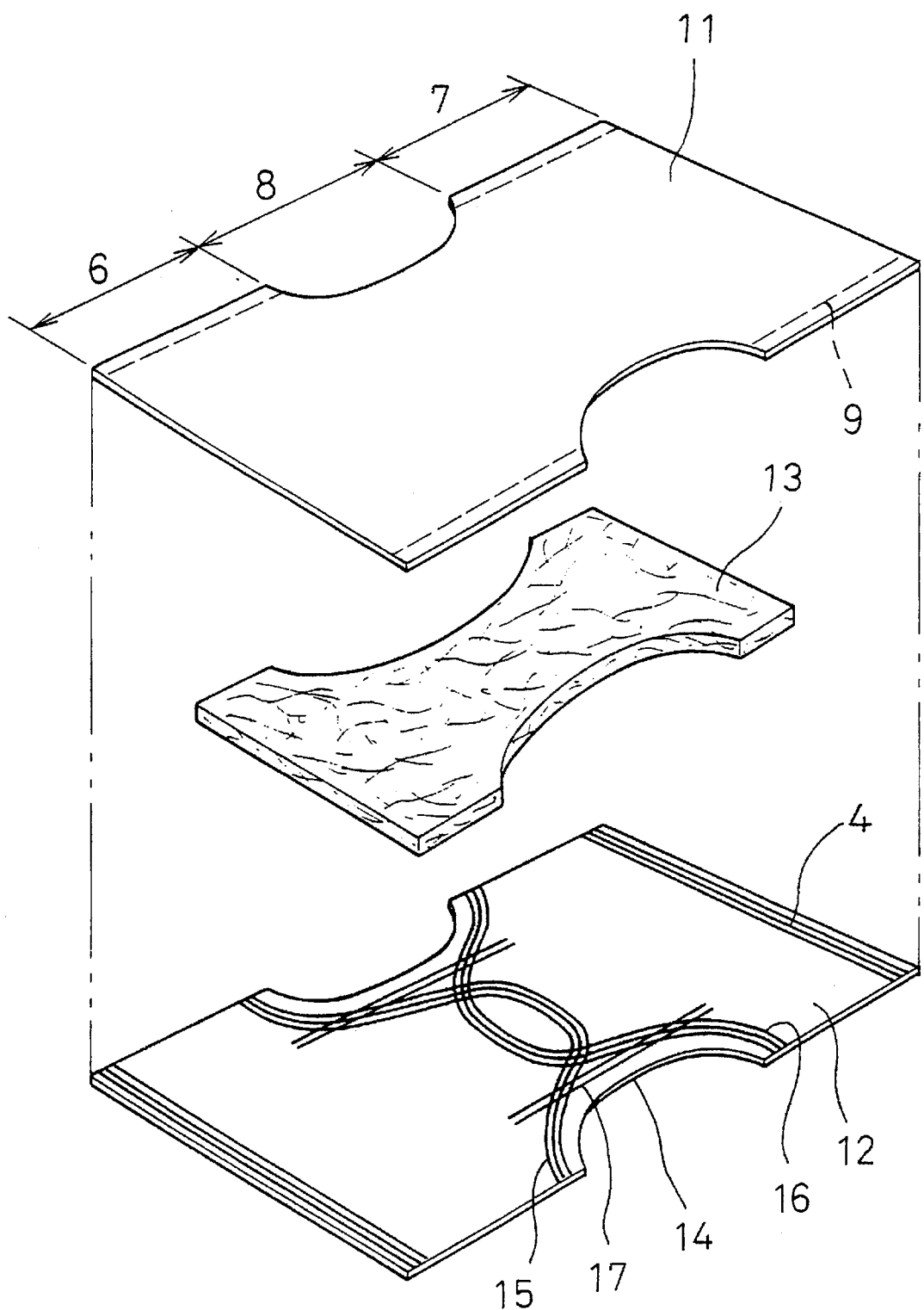
FIG. 2 is an exploded perspective view showing the diaper as longitudinally developed.

Referring to FIG. 2, the diaper 1 comprises, as viewed in the direction of thickness, a laminate including a liquid-permeable topsheet 11, a liquid-impermeable backsheet 12 and a liquid-absorbent core 13 disposed between these two sheets 11, 12. Portions of the top- and backsheets 11, 12 extending outward beyond a peripheral edge of the core 13 are water-tightly bonded together and the core 13 is intermittently bonded to at least one of the sheets 11, 12. The diaper 1 is longitudinally composed of the front and rear sections 6, 7 and a crotch section 8 interposed therebetween. The crotch section 8 is formed along transversely opposite sides with a pair of circular-arc-shaped notches destined to define leg surrounding edges 14, respectively. First, second and third elastic members 15, 16, 17 are attached by hot melt adhesive (not shown) to the inner surface of the backsheet 12 facing the topsheet 11 in association with the respective leg-hole defining edges 14. Of the first, second and third elastic members 15, 16, 17 each comprising single or plural elastic strings, the first and second elastic members 15, 16 are attached to the backsheet 12 with a tension at least along a pair of leg-hole defining edges 14 and the third elastic members 17 are attached to the backsheet 12 with a tension longitudinally of the diaper 1.

Figure 3:
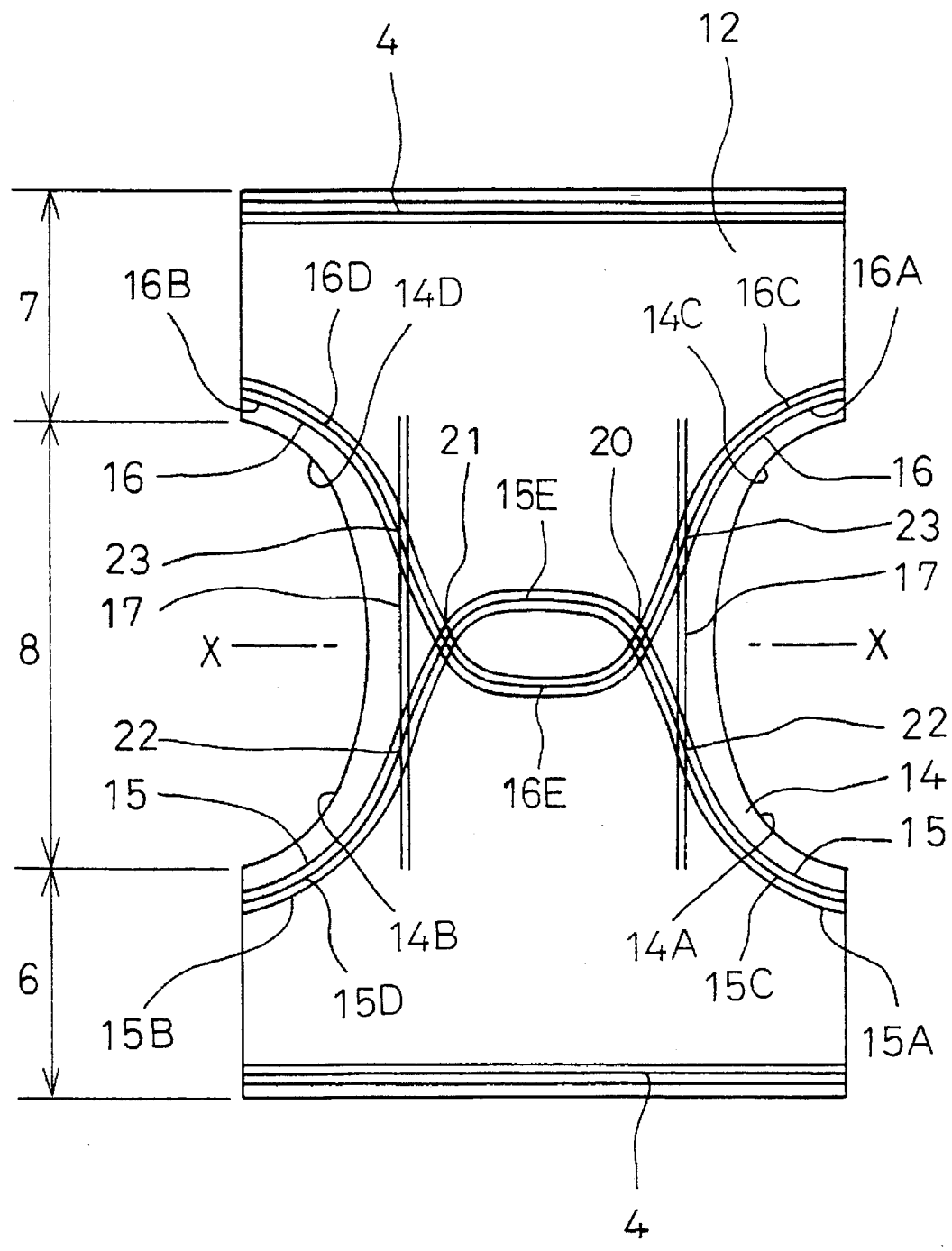
FIG. 3 is a plan view showing the first embodiment of an elastic arrangement used in the diaper of the invention.

Referring to FIG. 3, the first elastic member 15 comprises first and second front-half elastic portions 15C, 15D and an intermediate elastic portion 15E. The elastic portions 15C, 15D extend primarily along front-halves 14A, 14B of the leg-hole defining edges 14 and the elastic portion 15E extends across horizontally of the crotch section 8. Similarly, the second elastic member 16 comprises first and second front-half elastic portions 16C, 16D and an intermediate elastic portions 16E. The elastic portions 16C, 16D extend primarily along a rear-halves 14C, 14D of the leg-hole defining edges 14 and the elastic portion 16E extends across horizontally of the crotch section 8. Substantially in a central zone of the crotch section 8, the first and second elastic members 15, 16 describe a "U" and an "inverted U" and intersect each other at transversely opposite sides of the crotch section 8 to form intersecting points 20, 21. The third elastic members (bridging elastic portions) 17 extend longitudinally of the diaper 1 on the transversely opposite sides of the crotch section 8 and intersect the first and second elastic members 15, 16 to form intersecting points 23 lying slightly more adjacent to the respective side edges of the diaper 1 than the intersecting points 20, 21 are.

From its developed state, the diaper 1 having the first, second and third elastic members 15, 16, 17 attached thereto in the manner as described above is folded in two, with the topsheet 11 being inside, along a center line X—X (FIG. 3) which longitudinally divides the diaper 1 into two equal parts and then bonded together along the bonding lines 8. Thereupon, the leg-hole defining edges 14 respectively form the leg-holes 3 and simultaneously outer ends 15A, 15B of the first elastic member 15 are laid substantially upon the corresponding outer ends 16A, 16B of the second elastic member 16, resulting in that the first elastic member 15 cooperates with the second elastic member 16 to form the leg surrounding members 5 which are circumferentially elastic around the wearer's legs, respectively (FIG. 1). It should be noted here that the first and second elastic members 15, 16 describe at regions defined by the respective intersecting points 20, 21 and adjacent thereto "Vs outwardly opening sideways". These regions are relatively remote from the leg-hole defining edges and less contributive than the remaining region to desired fitness around the wearer's legs. However, the diaper 1 has the third elastic members 17 which extend adjacent the intersecting points 20, 21 and being elastic around the wearer's legs so as to compensate for above-mentioned insufficient contribution to the fitness around the wearer's legs. With the "Vs" each having an angle of opening less than 140°, the fitness around the wearer's legs will be unacceptably loosened, but the third elastic members 17 well compensate such inconvenience due to the small angle of opening and thereby rather enhance a barrier effect against leakage of body fluids.

Figure 4:
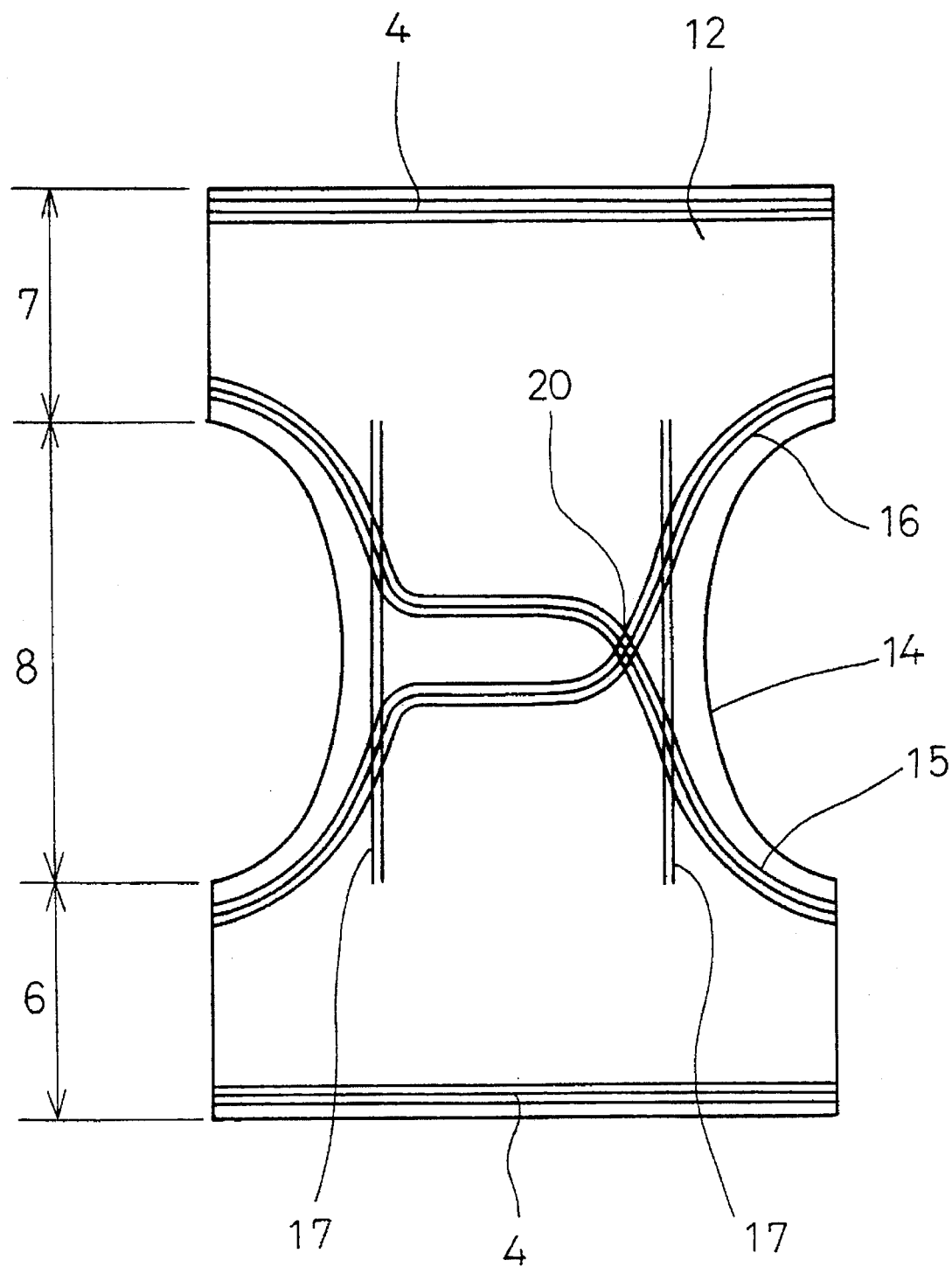
FIG. 4 is a view similar to FIG. 3, showing the second embodiment of the elastic arrangement.

Referring to FIG. 4, the first elastic member 15 extends along the front-half of the left leg-hole defining edge (right leg-hole defining edge as viewed in FIG. 4), then across the crotch section 8 and along the rear-half of the right leg-hole defining edge (left leg-hole defining edge as viewed in FIG. 4) and, similarly, the second elastic member 16 extends along the front-half of the right leg-hole defining edge, then across the crotch section 8 and along the rear-half of the left leg-hole defining edge, forming an intersecting point 20 adjacent the left leg-hole defining edge 14. The third elastic members 17 intersect the first and second elastic members 15, 16 in a central zone of the crotch section 8.

Figure 5:
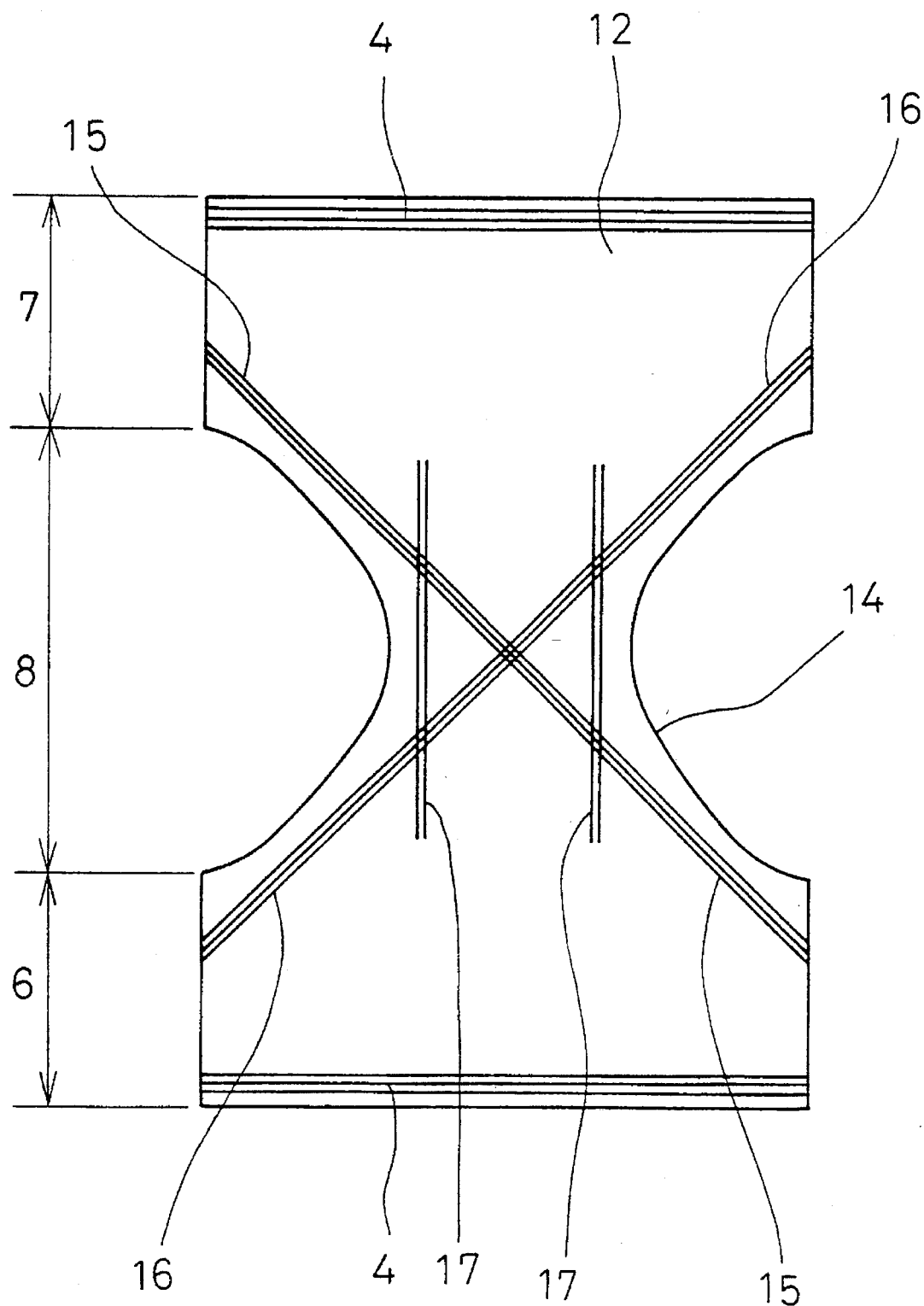
FIG. 5 is a view similar to FIG. 3, showing the third embodiment of the elastic arrangement.

Referring to FIG. 5, the substantially rectilinear first and second elastic members 15, 16 intersect each other to describe "X" and the third elastic members 17 intersect these first and second elastic members 15, 16 in a central zone of the crotch section 8.

Figure 6:
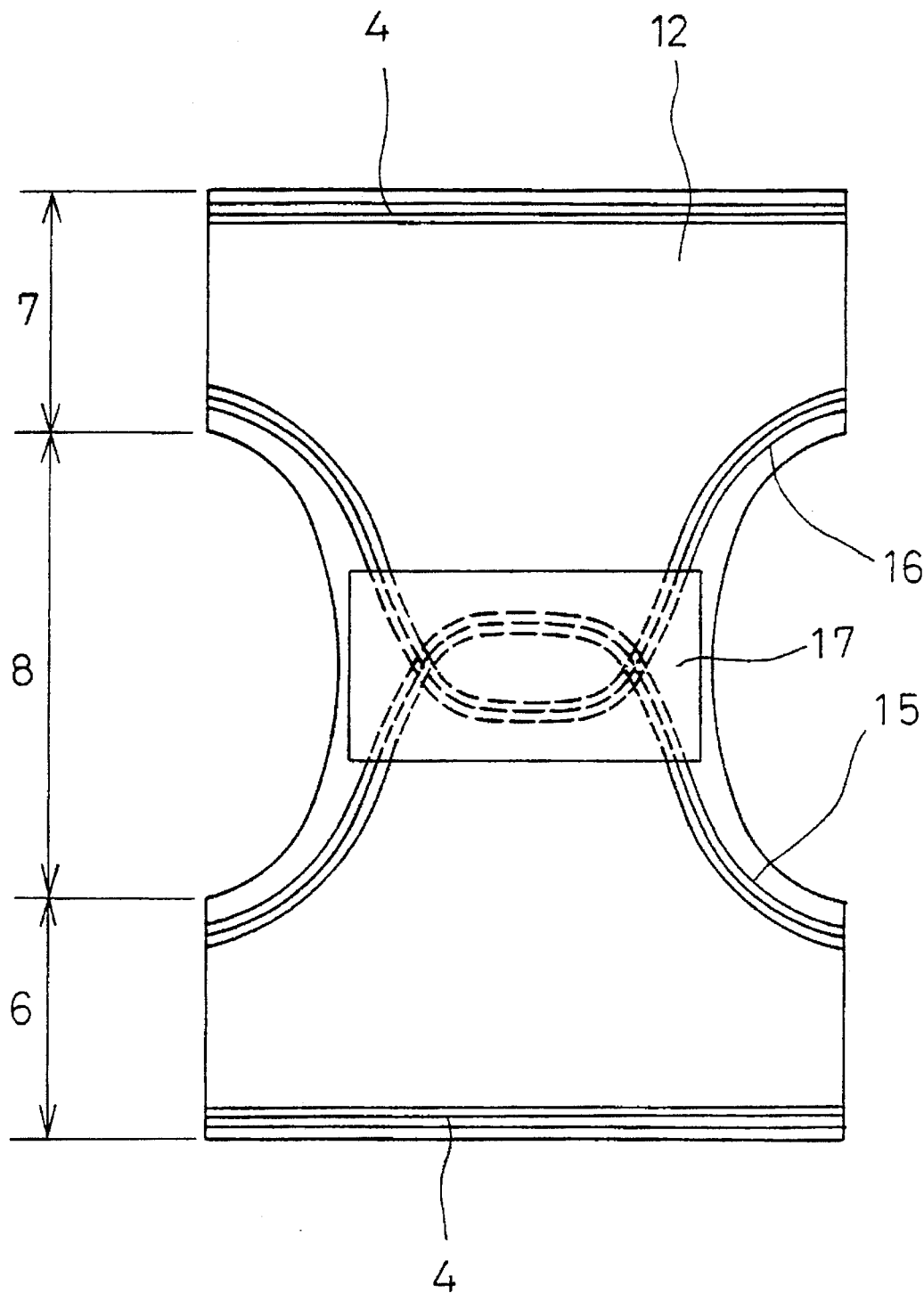
FIG. 6 is a view similar to FIG. 3, showing the fourth embodiment of the elastic arrangement.

Referring to FIG. 6, the third elastic member 17 in the form of a single elastic sheet is attached to the inner surface of the backsheet 12 with a tension longitudinally of the diaper 1. In this manner, the crotch section 8 of the diaper 1 is longitudinally contractible over a relatively large extent corresponding to the third elastic member 17 attached thereto and thereby comes in close contact with the wearer's crotch zone over the correspondingly large extent, effectively preventing body fluids from leaking sideways.

Figure 7:
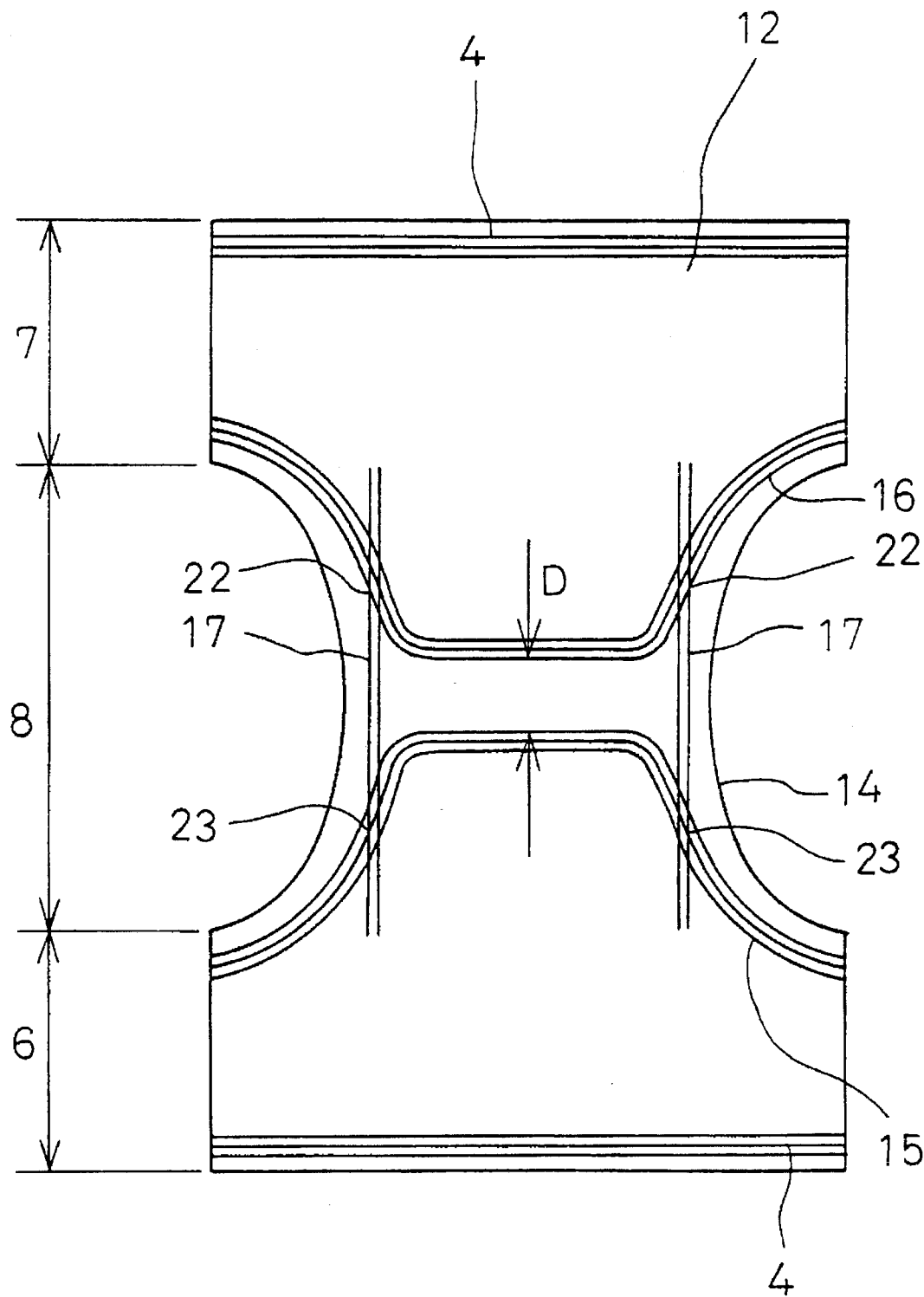
FIG. 7 is a view similar to FIG. 3, showing the fifth embodiment of the elastic arrangement.

Referring to FIG. 7, the first elastic member 15 extends primarily along a front-halves of the leg-hole defining edges 14 and crosses horizontally of the crotch section 8. Similarly, the second elastic member 16 extends primarily along a rear-halves of the leg-hole defining edges 14 and crosses horizontally of the crotch section 8. Substantially in a central zone of the crotch section 8, the first and second elastic members 15, 16 describe a "U" and an "inverted U" and are spaced from each other by a distance D in a central zone of the crotch section. The third elastic members 17 extend longitudinally of the diaper 1 on the transversely opposite sides of the crotch section 8 and intersect the first and second elastic members 15, 16 in the central zone of the crotch section to form intersecting points 22, 23. These first, second and third elastic members 15, 16, 17 cooperate with one another to surround the respective leg-hole defining edges.

Figure 8:
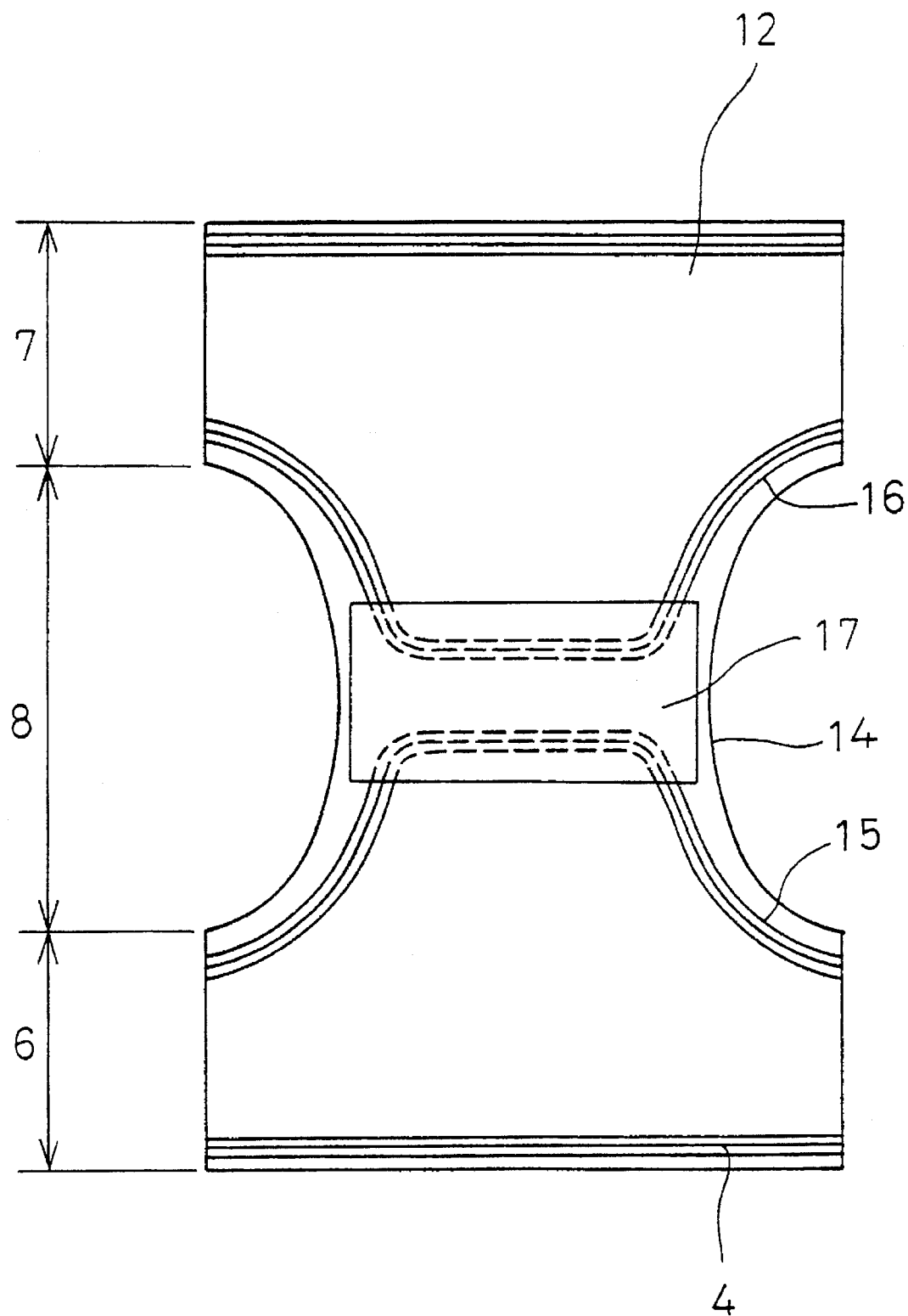
FIG. 8 is a view similar to FIG. 3, showing the sixth embodiment of the elastic arrangement.
Figure 9:
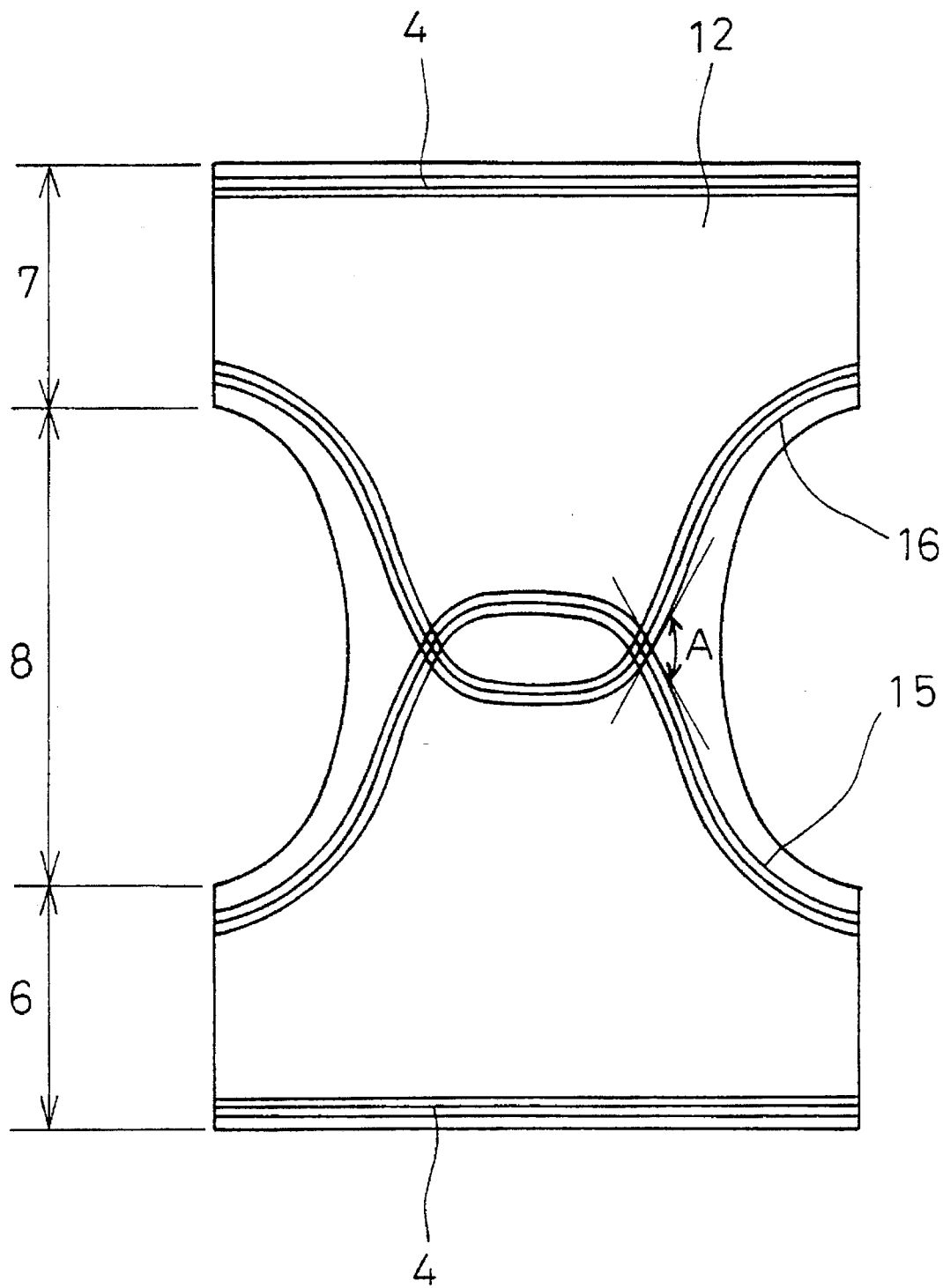

Referring to FIG. 8, the third elastic member 17 comprising a single stretchable sheet is bonded to the inner surface of the backsheet 12 with a tension longitudinally of the diaper 1 with longitudinally opposite side edges if the third elastic member 17 intersects the first and second elastic members 15, 16. A relatively wide area of the crotch section 8 over which the third elastic member 17 is bonded to the backsheet 12 of the diaper 1 is longitudinally stretchable so as to be put closely against a wearer's crotch and thereby to effectively prevent body fluids from leaking sideways.

Referring to a relationship between the core 13 and the third elastic members 17, the regions over which the third elastic members 17 are attached to the inner surface of the backsheet 12 are preferable to be spaced outward from transversely opposite side edges of the core 13 by an appropriate distance so that the elasticity of the third elastic members 17 might not be disturbed by a rigidity of the core 13 and the distance is preferably 5 mm or longer. It is not essential that the first and second elastic members 15, 16 extend across the crotch section 8 from the left to the right as exemplarily shown by FIGS. 3 through 6 and may be interrupted in the crotch section 8 or may be absent there. In such case, the first and second elastic members 15, 16 have their outer ends 15A, 15B, 16A, 16B at tops of the respective leg-holes 3 and their inner ends at bottoms of the respective leg-holes 3. With the arrangement of the first and second elastic members 15, 16 extending across the crotch section 8, the points at which the first and second elastic members 15, 16 extending away from the respective leg-hole defining edges 14 begin to approach the center line transversely dividing the diaper 1 in two equal parts may be referred to as their inner ends. While these inner ends lie on the longitudinal center line of the crotch section 8 in the illustrated embodiments, the inner ends may also be one-sided with respect to the longitudinal center line. While these first, second and third elastic members 15, 16, 17 are usually attached to the inner surface of the backsheet 12, it is also possible without departing from the scope of the invention to attach them to the topsheet 11, or to attach the first and second elastic members 15, 16 to the topsheet 11 and to attach the third elastic members 17 to the backsheet 12 or vice versa.

The undergarment according to the invention may be made from the materials conventionally used in the related industry. Bonding and attaching for assembly of these materials may be achieved by using the well known techniques of bonding and heat sealing.

With the undergarment according to the invention, the first and second front-half elastic portions (the first elastic member) and the first and second rear-half elastic portions (the second elastic member) attached to the front-halves and the rear-halves of the respective leg-hole defining edges so as to describe substantially circular arcs, respectively, intersect the third elastic members (bridging elastic portions) attached with a tension longitudinally of the diaper and thereby these elastic portions cooperate with one another to surround the wearer's legs under circumferential elasticity around the respective legs without interruption. Such unique arrangement allows body fluids from leaking sideways even if it is difficult for the first and second front-half elastic portions and the first and second rear-elastic portions to contract and stretch directly around the legs at their intersecting points and regions adjacent to these intersecting points.

What is claimed is:

1. An improved disposable absorbent undergarment comprising a liquid-permeable topsheet; a liquid-impermeable backsheet; a liquid-absorbent core between said topsheet and said backsheet; a laminate comprised of said topsheet, said backsheet and said core and having a front section, a rear section and a crotch section interposed between said front section and said rear section; first and second leg-hole defining edges in the form of generally circular-arc-shaped notches on transversely opposite sides of said crotch section; stretchable elastic members generally extending along each of said first and second leg-hole defining edges; and said elastic members comprising first and second front-half elastic portions extending primarily along first and second front-halves of said first and second leg-hole defining edges, first and second rear-half elastic portions extending primarily along first and second rear-halves of said first and second leghole defining edges, wherein the improvement comprises:

first and second bridging elastic portions respectively extending longitudinally on transversely opposite sides of said crotch section, said first and second front-half elastic portions connecting with each other in said crotch section, and said first and second rear-half elastic portions connecting with each other in said crotch section, said first bridging elastic portion intersecting said first front- and rear-half elastic portions, and said second bridging elastic portion intersecting said second front- and rear-half portions.

2. A disposable absorbent undergarment according to claim 1, wherein said first front- and rear-half elastic portions intersect each other in a longitudinally central zone on one of the transversely opposite sides of said crotch section, said second front- and rear-half elastic portions intersect each other in a longitudinally central zone on the other of the transversely opposite sides of said crotch section, said first bridging elastic portion is positioned outwardly of the intersecting point of said first front- and rear-half elastic portions, and said second bridging elastic portion is positioned outwardly of the intersecting point of said second front- and rear-half elastic portions.

3. A disposable absorbent undergarment according to claim 1, wherein said first and second front-half elastic portions and said first and second rear-half portions connect with each other between said first and second bridging elastic portions.

4. A disposable absorbent undergarment according to claim 1, wherein said first and second bridging elastic portions are in the form of a single elastic sheet.

5. A disposable absorbent undergarment according to claim 1, wherein said front-half elastic portions, said rear-half elastic portions and said bridging elastic portions comprise plural elastic strings.

* * * * *